United States Patent
Cagle et al.

(10) Patent No.: US 10,524,852 B1
(45) Date of Patent: Jan. 7, 2020

(54) DISTAL SEALING END EFFECTOR WITH SPACERS

(71) Applicant: Ethicon Endo-Surgery, Inc., Cincinnati, OH (US)

(72) Inventors: David J. Cagle, Cincinnati, OH (US); Donna L. Korvick, Maineville, OH (US); Eric N. Johnson, Maineville, OH (US)

(73) Assignee: Ethicon LLC, Guaynabo, PR (US)

(*) Notice: Subject to any disclaimer, the term of this patent is extended or adjusted under 35 U.S.C. 154(b) by 486 days.

(21) Appl. No.: 14/229,033

(22) Filed: Mar. 28, 2014

(51) Int. Cl.
*A61B 18/14* (2006.01)

(52) U.S. Cl.
CPC ................. *A61B 18/1445* (2013.01)

(58) Field of Classification Search
CPC .............. A61B 18/085; A61B 18/1442; A61B 18/1445; A61B 2018/00607; A61B 2018/1455
USPC ............................... 606/41, 50–52, 205, 207
See application file for complete search history.

(56) References Cited

U.S. PATENT DOCUMENTS

| | | | |
|---|---|---|---|
| 2,366,274 A | 1/1945 | Luth et al. | |
| 2,458,152 A | 1/1949 | Eakins | |
| 2,510,693 A | 6/1950 | Green | |
| 2,867,039 A | 1/1959 | Zach | |
| 3,166,971 A | 1/1965 | Stoecker | |
| 3,525,912 A | 8/1970 | Wallin | |
| 3,580,841 A | 5/1971 | Cadotte et al. | |
| 3,703,651 A | 11/1972 | Blowers | |
| 3,777,760 A | 12/1973 | Essner | |
| 4,005,714 A | 2/1977 | Hiltebrandt | |
| 4,034,762 A | 7/1977 | Cosens et al. | |
| 4,058,126 A | 11/1977 | Leveen | |
| 4,203,430 A | 5/1980 | Takahashi | |
| 4,220,154 A | 9/1980 | Semm | |
| 4,237,441 A | 12/1980 | van Konynenburg et al. | |
| 4,281,785 A | 8/1981 | Brooks | |

(Continued)

FOREIGN PATENT DOCUMENTS

| | | |
|---|---|---|
| DE | 4300307 A1 | 7/1994 |
| DE | 19608716 C1 | 4/1997 |

(Continued)

OTHER PUBLICATIONS

Covidien Brochure, [Value Analysis Brief], LigaSure Advance™ Pistol Grip, dated Rev. Apr. 2010 (7 pages).

(Continued)

*Primary Examiner* — Thomas A Giuliani

(57) ABSTRACT

A surgical end effector includes a cutting member, a first jaw, and a second jaw. The first jaw includes a first uninterrupted electrically conductive region. The second jaw includes an elongate slot extending longitudinally along a length of the second jaw member, the elongate slot defining a longitudinal axis aligned with the elongate slot. The second jaw also includes a second electrode surface extending between a proximal end and a distal end, the second electrode surface including a proximal interrupted electrically conductive region, a plurality of non-conductive stop members disposed on the proximal interrupted electrically conductive region, and a distal uninterrupted electrically conductive region distal to the proximal interrupted electrically conductive region.

9 Claims, 10 Drawing Sheets

(56) References Cited

U.S. PATENT DOCUMENTS

| | | |
|---|---|---|
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,312,023 A | 5/1994 | Green et al. |
| 5,318,563 A | 6/1994 | Malis et al. |
| 5,318,564 A | 6/1994 | Eggers |
| 5,318,589 A | 6/1994 | Lichtman |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A | 7/1996 | Strul et al. |
| 5,542,916 A | 8/1996 | Hirsch et al. |
| 5,558,671 A | 9/1996 | Yates |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman |
| 5,836,909 A | 11/1998 | Cosmescu |
| 5,836,943 A | 11/1998 | Miller, III |
| 5,836,990 A | 11/1998 | Li |
| 5,853,412 A | 12/1998 | Mayenberger |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,132,368 A | 10/2000 | Cooper |
| 6,144,402 A | 11/2000 | Norsworthy et al. |

(56) References Cited

U.S. PATENT DOCUMENTS

| | | |
|---|---|---|
| 6,152,923 A | 11/2000 | Ryan |
| 6,154,198 A | 11/2000 | Rosenberg |
| 6,162,208 A | 12/2000 | Hipps |
| 6,174,309 B1 | 1/2001 | Wrublewski et al. |
| 6,176,857 B1 | 1/2001 | Ashley |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,109 B1 | 5/2002 | Davison et al. |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,689 B1 | 10/2002 | Qin et al. |
| 6,464,702 B2 | 10/2002 | Schulze et al. |
| 6,480,796 B2 | 11/2002 | Wiener |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,551,309 B1 | 4/2003 | LePivert |
| 6,554,829 B2 | 4/2003 | Schulze et al. |
| 6,558,376 B2 | 5/2003 | Bishop |
| 6,562,037 B2 | 5/2003 | Paton et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,644,532 B2 | 11/2003 | Green et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,746,443 B1 | 6/2004 | Morley et al. |
| 6,752,815 B2 | 6/2004 | Beaupre |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,877,647 B2 | 4/2005 | Green et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 6,977,495 B2 | 12/2005 | Donofrio |
| 6,994,709 B2 | 2/2006 | Iida |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |

(56) References Cited

U.S. PATENT DOCUMENTS

| | | |
|---|---|---|
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,663 B2 | 8/2010 | Yates et al. |
| 7,784,663 B2 | 8/2010 | Shelton, IV |
| 7,789,883 B2 | 9/2010 | Takashino et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,058,771 B2 | 11/2011 | Giordano et al. |
| 8,061,014 B2 | 11/2011 | Smith et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |
| 8,357,158 B2 | 1/2013 | McKenna et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,598 B2 | 10/2013 | Falkenstein et al. |

(56) References Cited

U.S. PATENT DOCUMENTS

| | | |
|---|---|---|
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| D695,407 S | 12/2013 | Price et al. |
| 8,613,383 B2 | 12/2013 | Beckman et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,028,494 B2 | 5/2015 | Shelton, IV et al. |
| 9,028,519 B2 | 5/2015 | Yates et al. |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,125,662 B2 | 9/2015 | Shelton, IV |
| 9,149,324 B2 | 10/2015 | Huang et al. |
| 9,149,325 B2 | 10/2015 | Worrell et al. |
| 9,168,085 B2 | 10/2015 | Juzkiw et al. |
| 9,179,912 B2 | 11/2015 | Yates et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,277,962 B2 | 3/2016 | Koss et al. |
| 9,283,027 B2 | 3/2016 | Monson et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |
| 9,375,232 B2 | 6/2016 | Hunt et al. |
| 9,375,267 B2 | 6/2016 | Kerr et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 2002/0022836 A1 | 2/2002 | Goble et al. |
| 2002/0049551 A1 | 4/2002 | Friedman et al. |
| 2002/0107517 A1 | 8/2002 | Witt et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0054364 A1 | 3/2004 | Aranyi et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193148 A1 | 9/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0103819 A1 | 5/2005 | Racenet et al. |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0187547 A1* | 8/2005 | Sugi .................. A61B 18/1445 606/48 |
| 2005/0203507 A1 | 9/2005 | Truckai et al. |
| 2005/0256405 A1 | 11/2005 | Makin et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0058825 A1 | 3/2006 | Ogura et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0182322 A1 | 8/2006 | Bernhardt et al. |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton, IV et al. |
| 2007/0118115 A1 | 5/2007 | Artale et al. |
| 2007/0146113 A1 | 6/2007 | Truckai et al. |
| 2007/0173803 A1 | 7/2007 | Wham et al. |
| 2007/0173811 A1 | 7/2007 | Couture et al. |
| 2007/0173813 A1 | 7/2007 | Odom |
| 2007/0175949 A1 | 8/2007 | Shelton, IV et al. |

(56) References Cited

U.S. PATENT DOCUMENTS

| | | |
|---|---|---|
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0208340 A1 | 9/2007 | Ganz et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2007/0265616 A1 | 11/2007 | Couture et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0214967 A1 | 9/2008 | Aranyi et al. |
| 2008/0221565 A1 | 9/2008 | Eder et al. |
| 2008/0255642 A1 | 10/2008 | Zarins et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0099582 A1 | 4/2009 | Isaacs et al. |
| 2009/0112229 A1 | 4/2009 | Omori et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0171350 A1* | 7/2009 | Dycus ............... A61B 18/1445 606/48 |
| 2009/0182331 A1 | 7/2009 | D'Amelio et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0179545 A1* | 7/2010 | Twomey ............ A61B 18/1445 606/51 |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Horner |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0265196 A1 | 10/2012 | Turner et al. |
| 2012/0265241 A1 | 10/2012 | Hart et al. |
| 2012/0296371 A1 | 11/2012 | Kappus et al. |
| 2012/0323238 A1 | 12/2012 | Tyrrell et al. |
| 2013/0023925 A1 | 1/2013 | Mueller |
| 2013/0030428 A1 | 1/2013 | Worrell et al. |
| 2013/0030433 A1 | 1/2013 | Heard |
| 2013/0035685 A1 | 2/2013 | Fischer et al. |
| 2013/0079762 A1 | 3/2013 | Twomey et al. |
| 2013/0085496 A1 | 4/2013 | Unger et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0253502 A1 | 9/2013 | Aronow et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0194875 A1 | 4/2014 | Reschke et al. |
| 2014/0180281 A1 | 6/2014 | Rusin |
| 2014/0194915 A1 | 7/2014 | Johnson et al. |
| 2014/0214019 A1 | 7/2014 | Baxter, III et al. |
| 2014/0228844 A1 | 8/2014 | Hörlle et al. |
| 2014/0257284 A1 | 9/2014 | Artale |
| 2014/0316408 A1 | 10/2014 | Davison et al. |

(56) References Cited

U.S. PATENT DOCUMENTS

| | | |
|---|---|---|
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0045248 A1 | 2/2016 | Unger et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175028 A1 | 6/2016 | Trees et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |
| 2016/0317215 A1 | 11/2016 | Worrell et al. |

FOREIGN PATENT DOCUMENTS

| | | |
|---|---|---|
| DE | 29623113 U1 | 10/1997 |
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 0875209 B1 | 5/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 1728475 B1 | 8/2011 |
| EP | 2353518 A1 | 8/2011 |
| EP | 1767164 B1 | 1/2013 |
| EP | 2316359 B1 | 3/2013 |
| EP | 2578172 A2 | 4/2013 |
| EP | 2508143 B1 | 2/2014 |
| GB | 2472216 A | 2/2011 |
| JP | H 08-229050 A | 9/1996 |
| JP | 2008-018226 A | 1/2008 |
| JP | 5714508 B2 | 5/2015 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/062241 A1 | 8/2002 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/078051 A2 | 9/2004 |
| WO | WO 2004/112618 A2 | 12/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2006/119139 A2 | 11/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/102602 A2 | 7/2013 |

(56) References Cited

FOREIGN PATENT DOCUMENTS

WO    WO 2013/154157 A1    10/2013
WO    WO 2015/197395 A8    12/2015

OTHER PUBLICATIONS

Covidien Brochure, LigaSure Impact,™ Instrument LF4318, dated Feb. 2013 (3 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C.," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pp. (Jan. 1997), URL: http://www.mdconsult.com/das/article/body/156183648-2/jorg=journal&source=Ml&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, *Engineering Formulas* § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, *Integrated Circuit Engineering*, Addison-Wesley Publishing, Reading, MA (1979). (book—not attached).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, LigaSure Atlas™ Hand Switching Instruments, dated Dec. 2008 (2 pages).
Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S_D027541.
Jang, J. et al. "Neuro-fuzzy and Soft Computing." Prentice Hall, 1997, pp. 13-89, 199-293, 335-393,453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
U.S. Appl. No. 12/576,529, filed Oct. 9, 2009.

\* cited by examiner

DISTAL SEALING END EFFECTOR WITH SPACERS

BACKGROUND

The present invention relates to surgical instruments and, in various circumstances, to surgical sealing and transecting instruments.

BRIEF DESCRIPTION OF THE DRAWINGS

The features and advantages of this invention, and the manner of attaining them, will become more apparent and the invention itself will be better understood by reference to the following description of instances of the invention taken in conjunction with the accompanying drawings, wherein.

DETAILED DESCRIPTION

Figure 1:
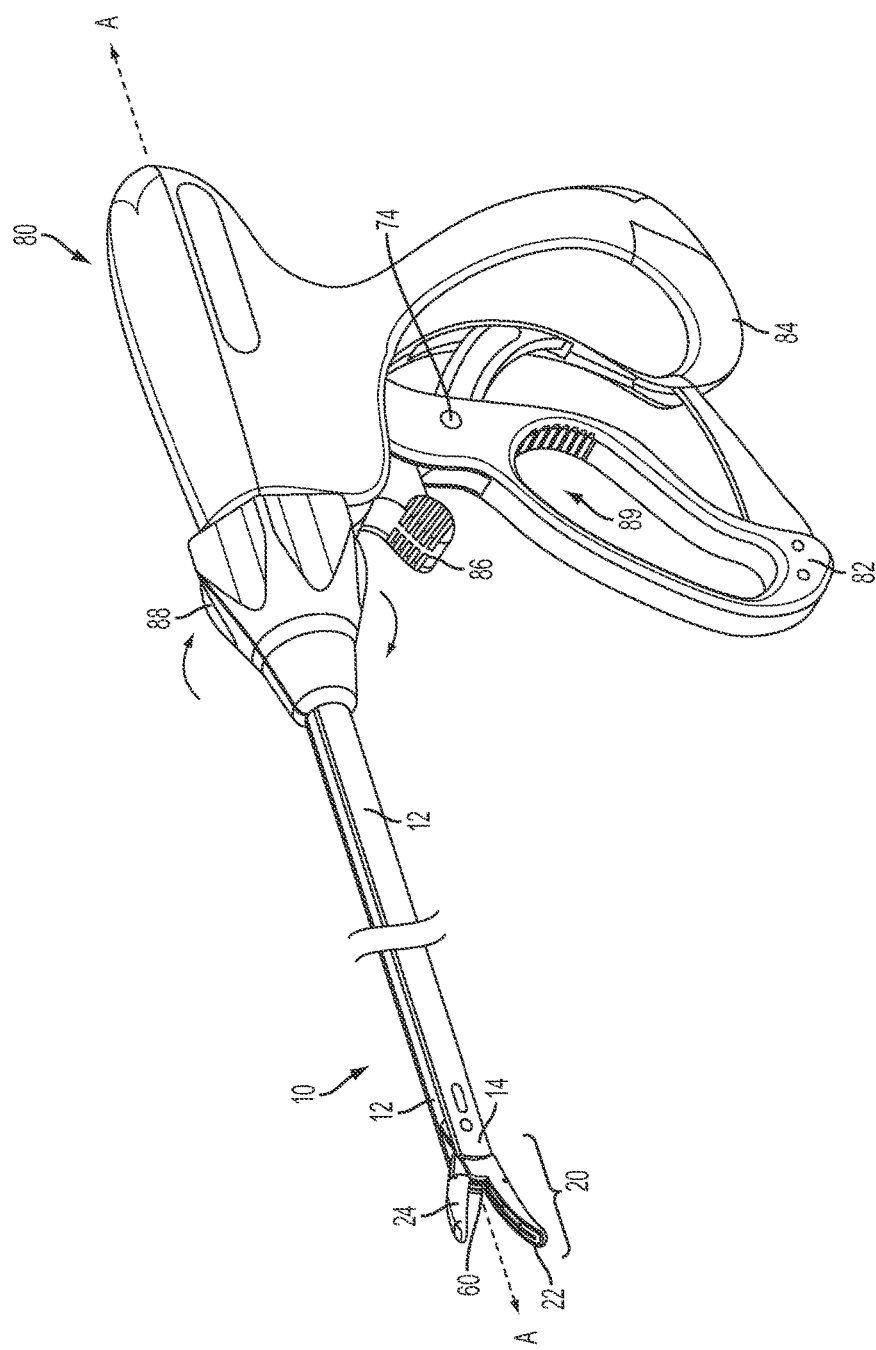
FIG. 1 illustrates a perspective view of a surgical instrument comprising a handle and an end effector assembly.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Turning to the Drawings wherein like numerals denote like components throughout the several views, FIG. 1 depicts an electrosurgical device 10 for use in various surgical procedures. The device 10 may include a handle assembly 80 and an end effector assembly 20. In certain instances, the device 10 may include a shaft 12 which has a distal end 14 dimensioned to mechanically engage with the end effector assembly 20 and a proximal end 16 (FIG. 2) which mechanically engages the handle assembly 80. As illustrated in FIG. 1, the end effector assembly 20 can be attached to the distal end 14 of shaft 12 and may include a pair of opposing jaw members 22 and 24; the handle assembly 80 can be attached to the proximal end 16 of shaft 12 and may include internally-disposed activating mechanisms, e.g., a movable handle 82 and a drive assembly 70, which mechanically cooperate to impart movement of the jaw members 22 and 24 from an open configuration wherein the jaw members 22 and 24 are disposed in a spaced relation relative to one another, to a clamping, closed, or approximated configuration wherein the jaw members 22 and 24 cooperate to grasp tissue therebetween, for example.

It is envisioned that the device 10 may be designed such that it is fully or partially disposable depending upon a particular purpose or to achieve a particular result. For example, end effector assembly 20 may be selectively and releasably engageable with the distal end 14 of the shaft 12 and/or the proximal end 16 of the shaft 12 may be selectively and releasably engageable with the handle assembly 80. In either of these two instances, the device 10 would be considered "partially disposable", i.e., a new or different end effector assembly 20 (or end effector assembly 20 and shaft 12) selectively replaces the old end effector assembly 20 as needed.

Figure 2:
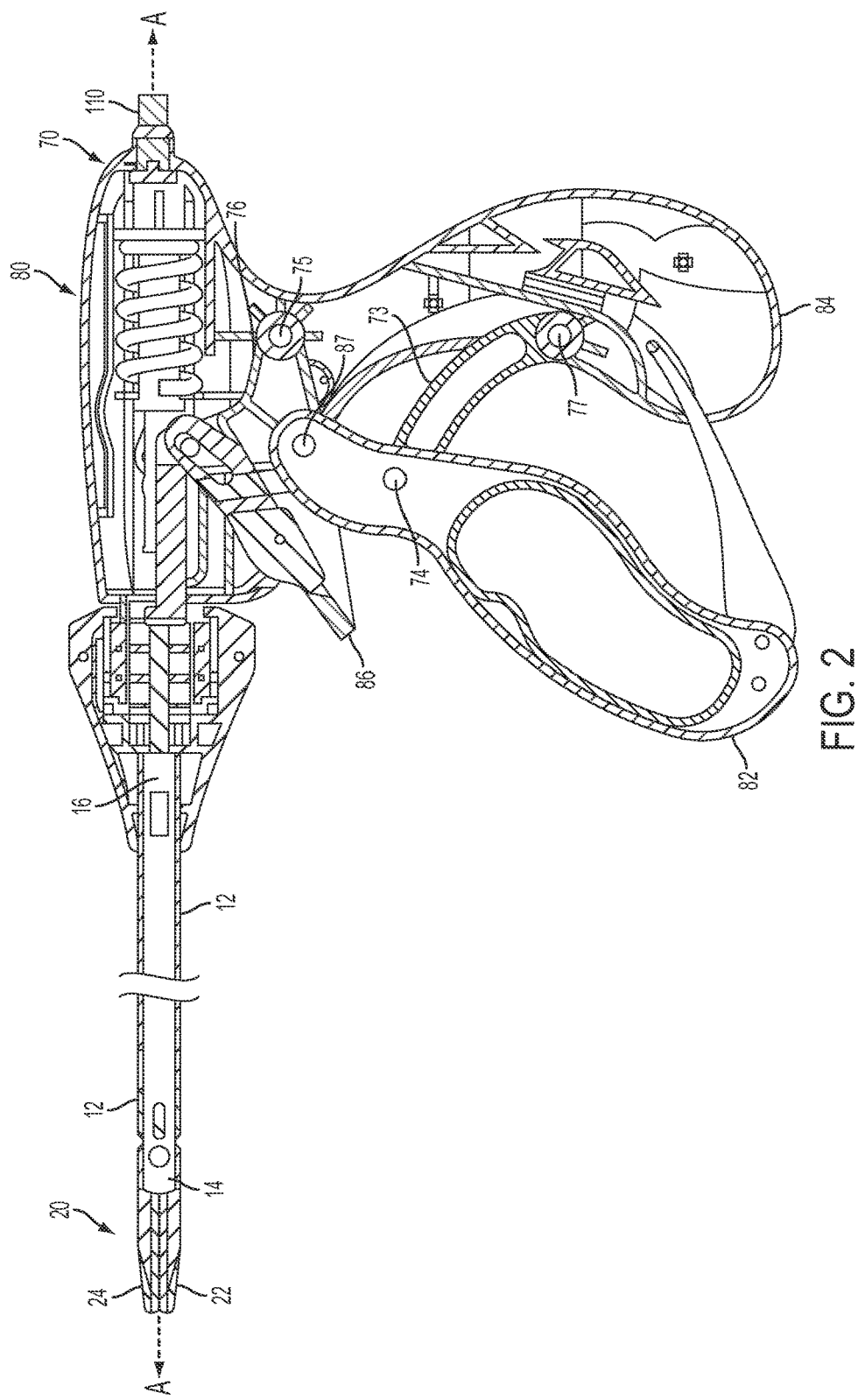
FIG. 2 illustrates a cross-section of the surgical instrument of FIG. 1 showing the internal working components of the handle and showing the end effector assembly in a closed configuration.

FIGS. 1 and 2 are taken from U.S. Pat. No. 7,473,253, entitled VESSEL SEALER AND DIVIDER WITH NON-CONDUCTIVE STOP MEMBERS, which issued on Jan. 6, 2009. FIGS. 1 and 2 illustrate exemplary operating elements and internal-working components of the handle assembly 80 which for the purposes of the present disclosure are generally described herein. The specific functions and operative relationships of these elements and the various internal-working components are described in more detail in U.S. Pat. No. 7,083,618, entitled VESSEL SEALER AND DIVIDER, which issued on Aug. 1, 2006. The entire disclosure of U.S. Pat. No. 7,083,618, entitled VESSEL SEALER AND DIVIDER, which issued on Aug. 1, 2006, is hereby incorporated by reference herein in its entirety. In addition, the entire disclosure of U.S. Pat. No. 7,473,253, entitled VESSEL SEALER AND DIVIDER WITH NON-CONDUCTIVE STOP MEMBERS, which issued on Jan. 6, 2009, is hereby incorporated by reference herein in its entirety. In addition, the entire disclosure of U.S. Pat. No. 7,491,201, entitled TISSUE SEALER WITH NON-CONDUCTIVE VARIABLE STOP MEMBERS AND METHOD OF SEALING TISSUE, which issued on Feb. 17, 2009, is hereby incorporated by reference herein in its entirety. In addition, the entire disclosure of U.S. Pat. No. 7,267,677, entitled VESSEL SEALING INSTRUMENT, which issued on Sep. 11, 2007, is hereby incorporated by reference herein in its entirety.

Referring again to FIGS. 1 and 2, the handle assembly 80 may include the movable handle 82 and a fixed handle 84. The movable handle 82 may include an aperture 89 defined therethrough which enables a user to grasp and move the handle 82 relative to the fixed handle 84, for example. In certain instances, the movable handle 82 can be selectively moveable about a pivot 87 from a first position relative to the fixed handle 84 to a second position in closer proximity to the fixed handle 84 which, as explained below, may impart relative movement of the jaw members 22 and 24 relative to one another.

In certain instances, the handle assembly 80 may house the drive assembly 70 which cooperates with the movable handle 82 to impart movement of the jaw members 22 and 24 from an open configuration wherein the jaw members 22 and 24 are disposed in spaced relation relative to one another, to a clamping, approximated, or closed configuration wherein the jaw members 22 and 24 cooperate to grasp tissue therebetween. In certain instances, the handle assembly 80 can generally be characterized as a four-bar mechanical linkage, for example, which may be composed of the following elements: movable handle 82, a link 73, a cam-like link 76 and a base link embodied by fixed pivot points 75 and 77.

Movement of the handle 82 may activate the four-bar linkage which, in turn, may actuate the drive assembly 70 for imparting movement of the opposing jaw members 22 and 24 relative to one another to grasp tissue therebetween. Other drive assemblies for moving at least one of the jaw members 22 and 24 relative to the other one of the jaw members 22 and 24 are contemplated by the present disclosure. In certain instances, one of the jaw member 22 and 24 can be fixed relative to the shaft 12 such as, for example, the jaw member 22; in such instances, the jaw member 24 can be movable relative to the jaw member 22 between the open configuration and the closed, clamped, or approximated configuration by advancing and retracting a reciprocating member which is operably coupled to the jaw member 24 and the movable handle 82, for example. The operation of the various working components of the drive assembly 70 are explained in detail in the above-mentioned U.S. Pat. No. 7,083,618, for example. Once the tissue is grasped between opposing jaw members 22 and 24, electrosurgical energy can be supplied to the jaw members 22 and 24 through an electrosurgical interface 110 disposed within the handle 84 as explained in more detail the above-mentioned U.S. Pat. No. 7,083,618, for example. In various instances, as illustrated in FIG. 1, the device 10 may include a trigger 86 which reciprocates a cutting member 60 disposed within the end effector assembly 20. Once a tissue seal is formed, the user can activate the trigger 86 to transect the sealed tissue.

Figure 3:
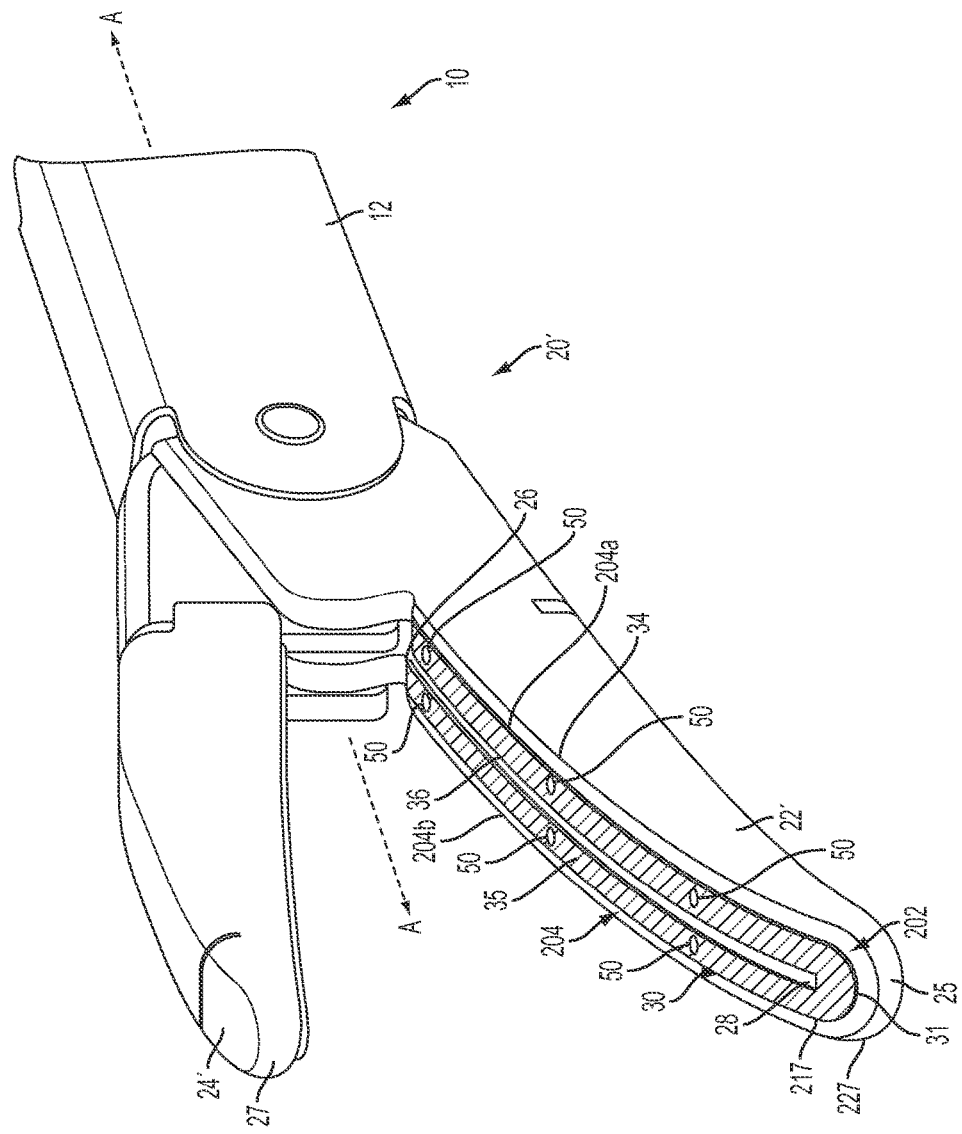
FIG. 3 illustrates a perspective view of an end effector assembly of the surgical instrument of FIG. 1.

Referring to FIG. 3, the device 10 may comprise an end effector assembly 20' which may replace the end effector assembly 20. The end effector assembly 20' can be similar in many respects to the end effector assembly 20. In certain instances, the end effector assembly 20' may include jaw members 22' and 24' which are similar in many respects to the jaw members 22 and 24, respectively. For example, the jaw members 22' and 24' can be operable to capture tissue in a similar manner to the jaw members 22 and 24. In certain instances, as illustrated in FIG. 3, the end effector assembly 20' may extend along a curved path. In result, distal ends 25 and 27 of the jaw members 22' and 24', respectively, may deviate to the right or to the left from a longitudinal axis A-A, as illustrated in FIG. 3, for example.

In certain instances, each of the jaw members 22' and 24' may include an electrically conductive sealing surface 35 dispose on an inner-facing surface 30 thereof and an insulator 34. It is envisioned that the electrically conductive surfaces 35 cooperate to seal tissue held therebetween upon the application of electrosurgical energy. In certain instances, the electrically conductive sealing surfaces 35 may also include a pinch trim which facilitates secure engagement of the electrically conductive surfaces 35 to the insulators 34 and also simplifies the overall manufacturing process, for example. In certain instances, a least one of the electrically conductive surfaces 35 of the jaw members, e.g., 22', may include a longitudinally-oriented channel 36 defined therein which may extend longitudinally along a length of the jaw member 22', for example. It is envisioned that the channel 36 facilitates longitudinal reciprocation of the cutting member 60. In certain instances, the elongate slot 36 may include a distal end 28; the cutting member 60 can be advanced distally through the elongate slot 36 up to the distal end 28.

In use, a clinician may place the end effector assembly 20' and close the jaws members 22' and 24' around a tissue bite to be acted upon, for example, by pivoting the movable handle 82, as described above. Once the tissue bite is secure between the jaw members 22' and 24', energy may flow between the electrically conductive surfaces 35 and through the captured tissue. The provision of energy may be accomplished in any suitable way. See, for example, U.S. Patent Publication No. 2011/0087216 A1, entitled SURGICAL GENERATOR FOR ULTRASONIC AND ELECTROSURGICAL DEVICES, and filed Oct. 1, 2010, the entire disclosure of which is hereby incorporated by reference herein.

Figure 6:
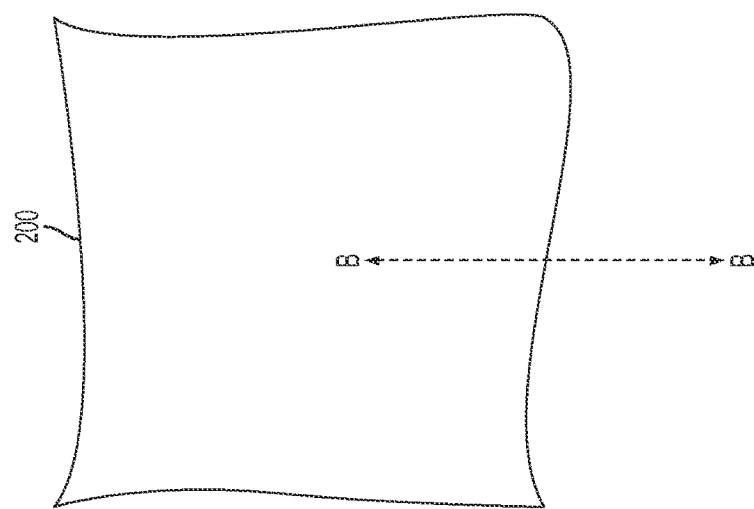
FIG. 6 illustrates a top view of the tissue of FIG. 4 showing two segments transected and sealed along the axis B-B by the end effector assembly of FIG. 3.
Figure 5:
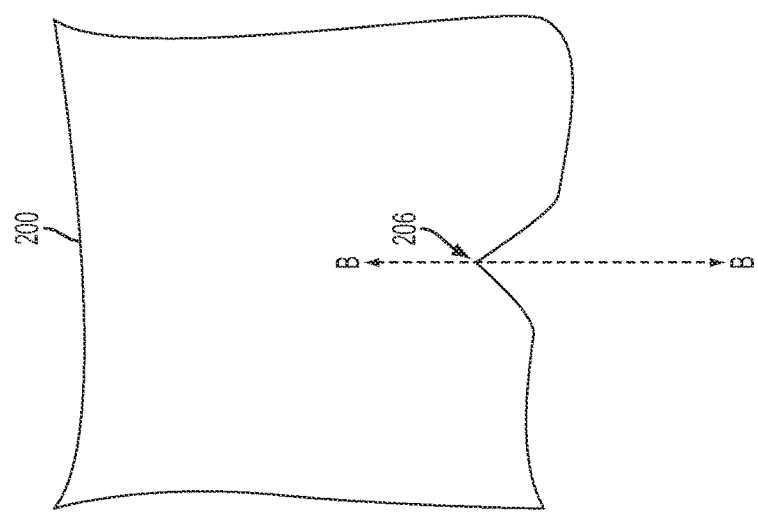
FIG. 5 illustrates a top view of the tissue of FIG. 4 showing a segment transected and sealed along an axis B-B by the end effector assembly of FIG. 3.
Figure 4:
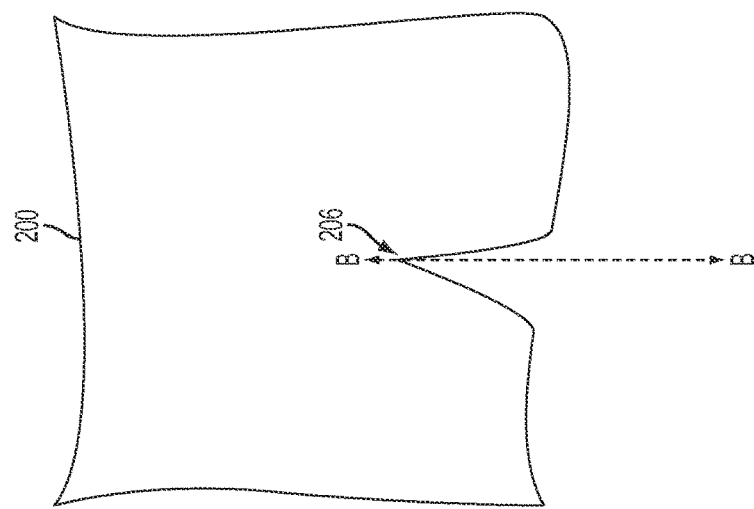
FIG. 4 illustrates a top view of tissue.

Referring to FIGS. 3-6, in certain instances, the end effector assembly 20' may be configured to seal and transect or cut a large tissue 200 such as, for example, Mesentery tissue. As illustrated in FIGS. 4-6, the end effector assembly 20' may seal and transect the large tissue 200 in segments along an axis B-B, for example. In certain instances, the jaw members 22' and 24' can be large jaw members suitable for sealing and transecting large segments tissue to reduce the total number of segments to be sealed and transected by the device 10 in order to seal and transect the large tissue. In certain instances, the jaw members 22' and 24' may each comprise any length selected from a range of about 15 mm, for example, to about 30 mm, for example. In certain instances, the jaw members 22' and 24' may each comprise a length of about 20 mm, for example. Other ranges for the lengths of the large jaw members 22' and 24' are contemplated by the present disclosure.

In certain instances, the end effector assembly 20' may be configured to seal and transect small tissue, for example. In such instances, the jaw members 22' and 24' can be small jaw members suitable for sealing and transecting the small tissue. For example, in certain instances, the jaw members 22' and 24' may each comprise any length selected from a range of about 5 mm, for example, to about 10 mm, for example. Other ranges for the lengths of the small jaw members 22' and 24' are contemplated by the present disclosure.

Referring again to FIG. 3, in certain instances, at least one jaw member 22' and/or 24' may include one or more stop members 50 which may limit the movement of the two opposing jaw members 22' and 24' relative to one another. In certain instances, the stop members 50 may extend from the sealing surface or tissue contacting surface 35 a predetermined distance according to the specific material properties (e.g., compressive strength, thermal expansion, etc.) to yield a consistent and accurate gap distance between the two opposing jaw members 22' and 24'. In certain instances, the gap distance maintained by the stop members 50 between opposing sealing surfaces 35 may range from about 0.001 inches, for example, to about 0.005 inches, for example. In certain instances, the gap distance may range from about 0.002 inches, for example, to about 0.003 inches, for example.

In certain instances, the stop members 50 can be made from one or more electrically insulative or non-conductive materials such as, for example, parylene, nylon and/or ceramic. It is envisioned that the stop members 50 may be disposed on one or both of the jaw members 22' and 24' in various configurations and arrangements to prevent short circuiting of the jaw members 22' and 24' and/or enhance the gripping characteristics of the jaw members 22' and 24' during sealing and transecting, for example. In certain instances, the stop members 50 may comprise various shapes and geometries such as, for example, a cylindrical shape and/or a circle-like cross-section. It is envisioned that the stop members 50 can be substantially equal in size; however, one or more of the stop members 50 may be dimensioned larger or smaller than the other stop members, for example.

In certain instances, the stop members 50 can be molded onto the jaw members 22' and 24' (e.g., over-molding, injection molding, etc.), stamped onto the jaw members 22' and 24' or deposited onto the jaw members 22' and 24', for example. Stamping is defined herein to encompass virtually any press operation known in the trade, including but not limited to: blanking, shearing, hot or cold forming, drawing, bending, and coining. In certain instances, the stop members 50 can extend from one or both of the electrically conductive surfaces 35 of the jaw members 22' and 24, for example. In certain instances, the stop members 50 can be attached to the electrically conductive surfaces 35 in a snap-fit manner, for example. Alternatively, the stop members 50 can be molded onto the electrically conductive surfaces 35, for example. Alternatively, the stop members 50 can be adhered to the electrically conductive surfaces 35 by any suitable adhesive, for example. Other techniques for positioning the stop members 50 with respect to the electrically conductive surfaces 35 are contemplated by the present disclosure.

In certain instances, the stop members 50 can be created by thermally spraying a ceramic material onto the surface of the jaw member 22' and 24' to form the stop members 50, for example. Several thermal spraying techniques are contemplated which involve depositing a broad range of heat resistant and insulative materials on the electrically conductive surfaces 35 to create stop members 50 such as High velocity Oxy-fuel deposition and plasma deposition, for example.

Figure 7:
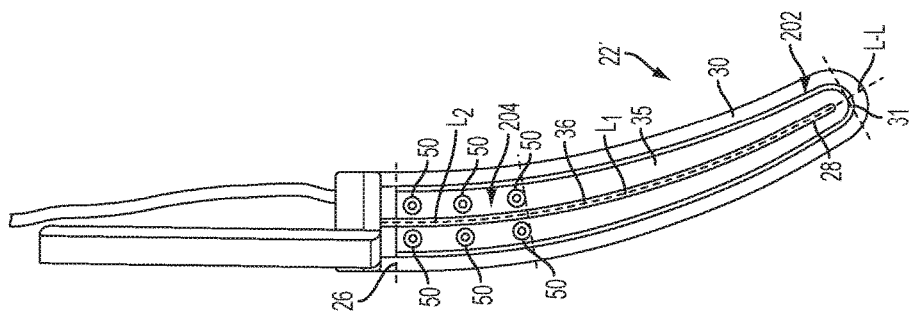
FIG. 7 illustrates a top view of a jaw member of the end effector assembly of FIG. 3.

Referring to FIG. 7, an exemplary embodiment of the jaw member 22' is illustrated. For illustration purposes, the following disclosure describes the construction and features of the jaw member 22'. For conciseness and clarity of disclosure, a detailed description of the construction and features of the jaw member 24' is omitted, it being understood that the jaw member 24' may comprise the same, or a similar, construction and features as the jaw member 22'. In certain instances, as illustrated in FIG. 7, the electrically conductive surface 35 of the jaw member 22' may include a distal electrically conductive region 202 and a proximal electrically conductive region 204. In certain instances, the proximal electrically conductive region may comprise a plurality of the stop members 50 which can be disposed on the proximal electrically conductive region 204 and may interrupt energy flow between the proximal electrically conductive region of the jaw member 22' and a corresponding electrically conductive region of the jaw member 24'. In certain instances, the proximal electrically conductive region 204 can be bifurcated into a first proximal electrically conductive region 204a and a second proximal electrically conductive region 204b by the passing of the elongate slot 36 therethrough, as illustrated in FIG. 7. In certain instances, the stop members 50 can be disposed onto the first proximal electrically conductive region 204a and the second proximal electrically conductive region 204b, for example. In certain instances, the distal electrically conductive region 202 can be defined by the lack or absence of interrupters that interrupt energy flow to or from the electrically conductive surface 35 of the distal electrically conductive region 202, for example. In certain instances, the distal electrically conductive region 202 can be defined by the lack or absence of stop members on the electrically conductive surface 35 of the distal electrically conductive region 202, for example.

In certain instances, as illustrated in FIG. 7, the distal electrically conductive region 202 can be an uninterrupted electrically conductive region permitting uninterrupted energy flow between the distal electrically conductive region 202 of the jaw member 22' and a corresponding uninterrupted electrically conductive region of the jaw member 24' through the tissue captured therebetween, for example. In certain instances, as illustrated in FIG. 5, a sealed and transected segment of tissue such as, for example, the tissue 200 may comprise a distal end portion 206 which can be subject to significant tension forces due, in part, to its terminal position. In certain instances, the uninterrupted flow of energy between the distal electrically conductive region 202 of the jaw member 22' and the corresponding uninterrupted electrically conductive region of the jaw member 24' may provide a sufficiently secure seal at the distal end portion 206 to prevent or significantly reduce bleeding by creating an uninterrupted seal at the distal end portion 206. In certain instances, the uninterrupted seal may significantly reduce the instance of a fracture at the distal end portion 206 post sealing which may prevent or significantly reduce the instance of renewed bleeding, for example.

In certain instances, the surface area of the distal uninterrupted electrically conductive region 202 can be about one quarter, for example, of the surface area of the proximal interrupted electrically conductive region 204. The reader will appreciate that the surface area of the distal uninterrupted electrically conductive region 202 can determine the size, quality, and/or shape of the seal at the distal end portion 206 of the tissue 200. In certain instances, the surface area of the distal uninterrupted electrically conductive region 202 can be about one third, for example, of the surface area of the proximal interrupted electrically conductive region 204. In certain instances, the surface area of the distal uninterrupted electrically conductive region 202 can be about one half, for example, of the surface area of the proximal interrupted electrically conductive region 204. In certain instances, the surface area of the distal uninterrupted electrically conductive region 202 can be equal, or at least substantially equal, to the surface area of the proximal interrupted electrically conductive region 204, for example. In certain instances, the ratio of the surface area of the distal uninterrupted electrically conductive region 202 to the surface area of the proximal interrupted electrically conductive region 204 may be any value selected from a range greater than or equal to about one fifth, for example, and less than or equal to about one, for example.

Figure 8:
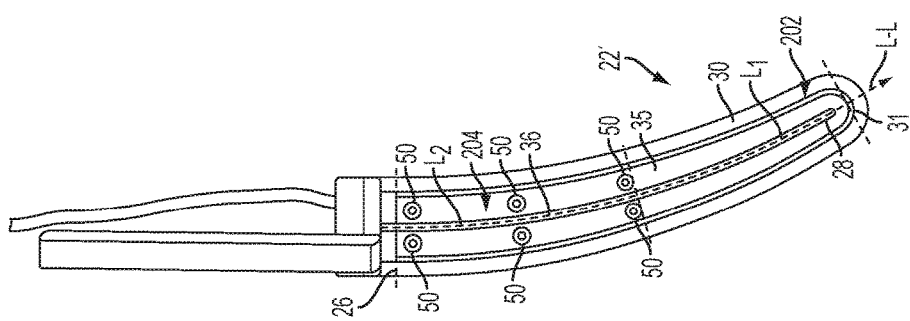
FIG. 8 illustrates a top view of a jaw member of the end effector assembly of FIG. 3.
Figure 9:
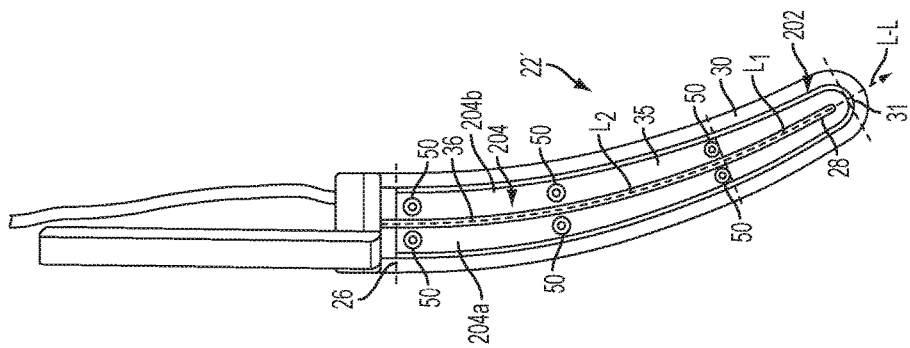
FIG. 9 illustrates a top view of a jaw member of the end effector assembly of FIG. 3.

Referring to FIGS. 7-9, in certain instances, the surface 35 of the jaw member 22' may extend between a proximal end 26 and a distal end 31. In certain instances, the distal uninterrupted electrically conductive region 202 may comprise a length L1 extending proximally from the distal end 31; and the proximal interrupted electrically conductive region 204 may comprise a length L2 extending distally from the proximal end 26 and residing proximal to the length L1, for example. In certain instances, the lengths L1 and L2 may extend along an axis L-L which can be aligned with the elongate slot 36, for example. In certain instances, the ratio of the length L1 to the length L2 can be any value selected from a range greater than or equal to about one fifth, for example, and less than or equal to about two, for example. In certain instances, the length L1 can be about one half, for example, of the length L2. In certain instances, the length L1 can be about one quarter, for example, of the length L2. In certain instances, as illustrated in FIG. 7, the length L1 can be about one fifth, for example, of the length L2.

Figure 10:
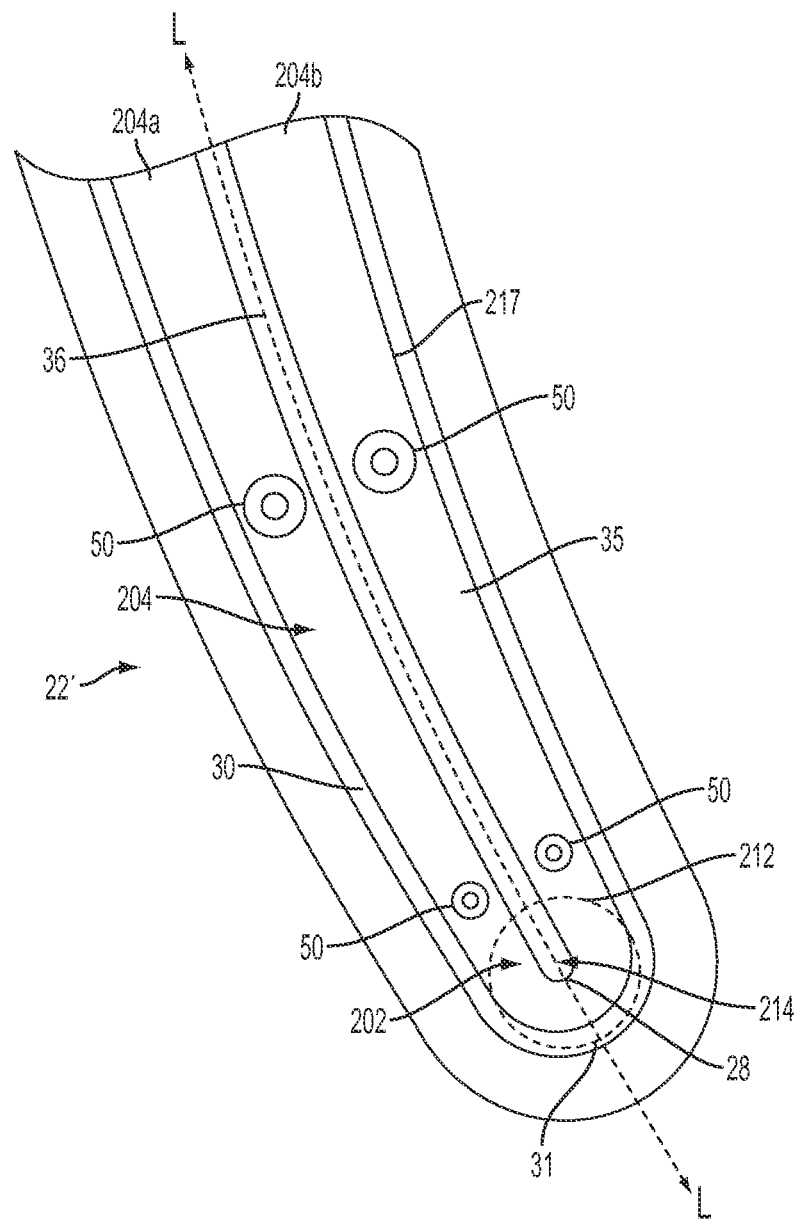
FIG. 10 illustrates a partial top view of a jaw member of the end effector assembly of FIG. 3.
Figure 11:
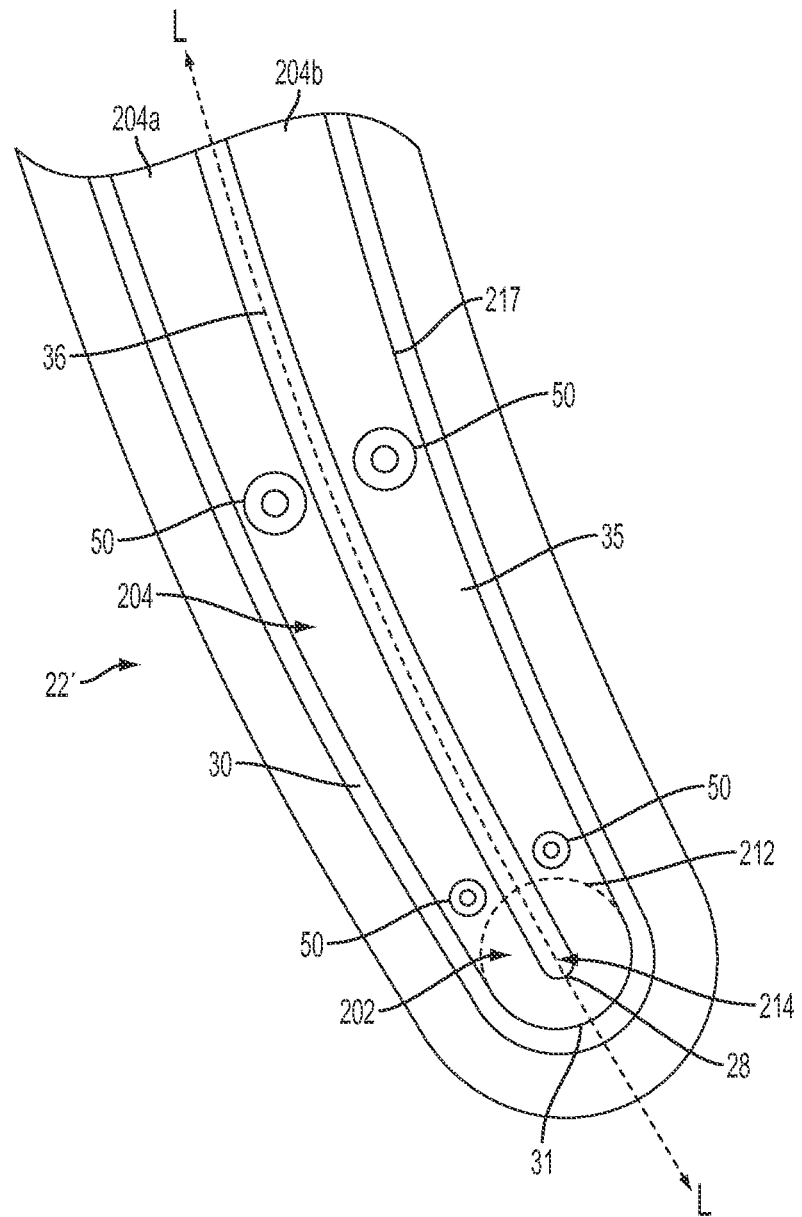
FIG. 11 illustrates a partial top view of a jaw member of the end effector assembly of FIG. 3.

Referring to FIGS. 10 and 11, in certain instances, the distal uninterrupted electrically conductive region 202 can be defined by a circular perimeter 212, for example. It is envisioned that the circular perimeter 212 may encompass the distal uninterrupted electrically conductive region 202. In certain instances, the circular perimeter 212 may have a radius comprising a length that is about double the distance between the distal end 28 of the elongate slot 36 and the distal end 31 of the electrically conductive surface 35, for example. In certain instances, the circular perimeter 212 may encompass a distal portion 214 of the elongate slot 36, as illustrated in FIG. 10, for example. In certain instances, as illustrated in FIG. 11, the distal end 31 of the electrically conductive surface 35 may be located on the circular perimeter 212, for example. In certain instances, the circular perimeter 212 may have a radius comprising a length that is about triple the distance between the distal end 28 of the elongate slot 36 and the distal end 31 of the electrically conductive surface 35, for example. In certain instances, the circular perimeter 212 may have a radius comprising a length that is about quadruple the distance between the distal end 28 of the elongate slot 36 and the distal end 31 of the electrically conductive surface 35, for example.

Figure 12:
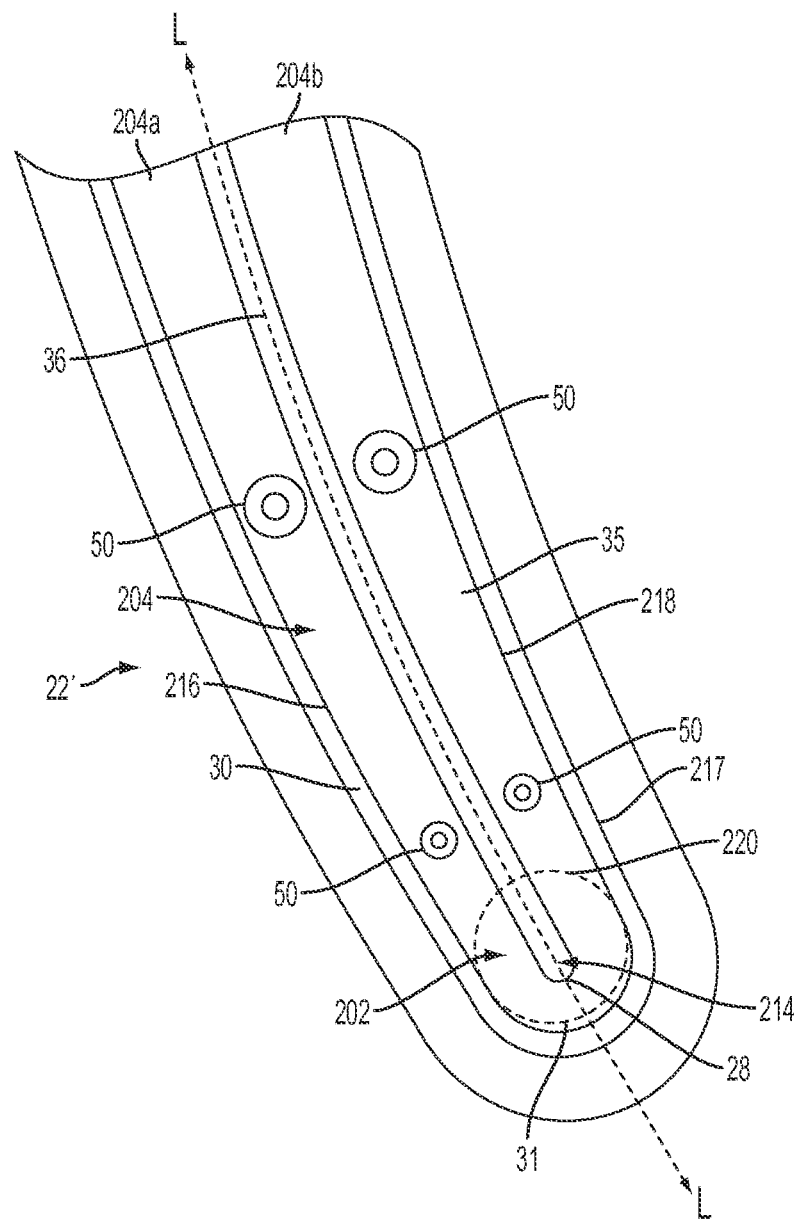
FIG. 12 illustrates a partial top view of a jaw member of the end effector assembly of FIG. 3.
Figure 13:
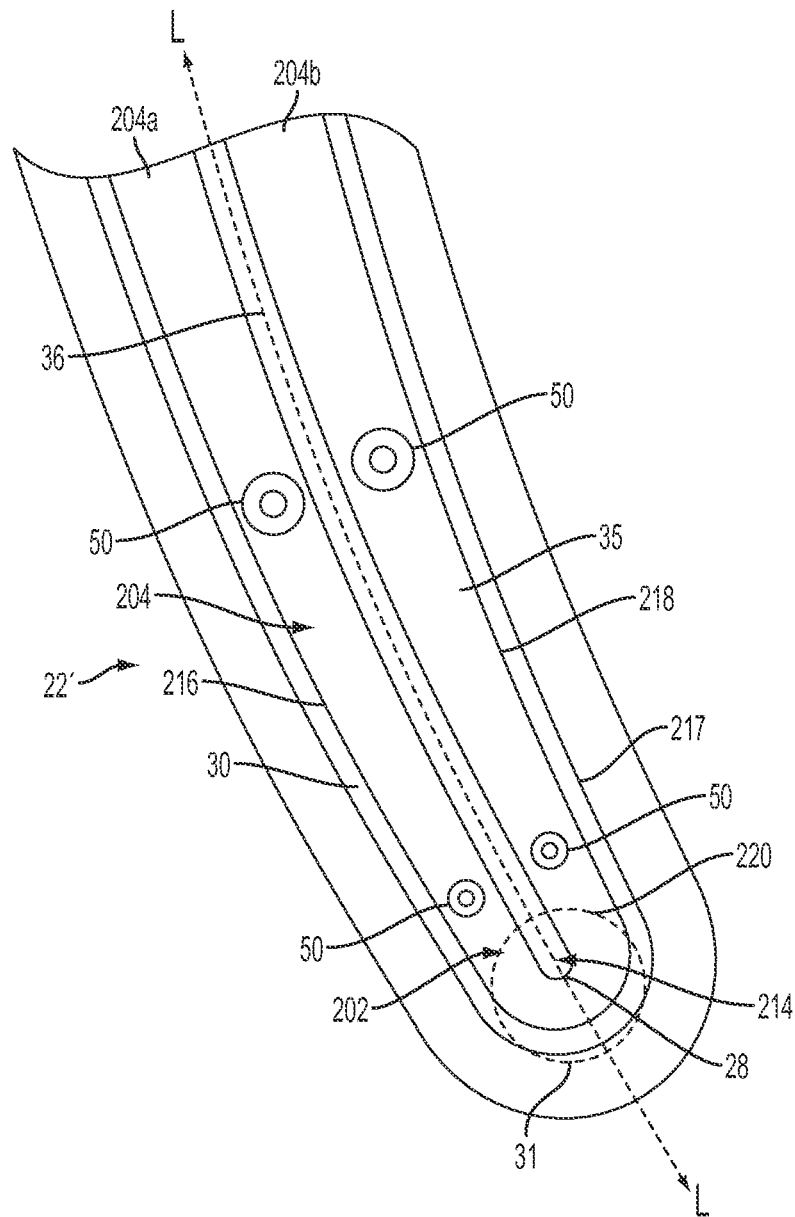
FIG. 13 illustrates a partial top view of a jaw member of the end effector assembly of FIG. 3.

Referring to FIGS. 12 and 13, in certain instances, the first proximal electrically conductive region 204*a* may include a peripheral point on an outer perimeter 217 of the electrically conductive surface 35 on a first lateral side of the elongate slot 36 such as, for example, peripheral point 216. In certain instances, the second proximal electrically conductive region 204*b* may include a peripheral point on the outer perimeter 217 on a second lateral side, opposite the first lateral side, of the elongate slot 36 such as, for example, peripheral point 218. In certain instances, the distal uninterrupted electrically conductive region 202 can be defined by a circular perimeter 220, for example. It is envisioned that the circular perimeter 220 may encompass the distal uninterrupted electrically conductive region 202. In certain instances, the circular perimeter 220 may have a diameter comprising a length that is equal, or at least substantially equal, to the distance between the peripheral point 216 and the peripheral point 218, for example. In certain instances, the circular perimeter 220 may encompass the distal end 28 of the elongate slot 36, as illustrated in FIG. 12. In certain instances, the circular perimeter 220 may encompass the distal end 31 of the electrically conductive surface 35, as illustrated in FIG. 13. In certain instances, as illustrated in FIG. 13, the distal end 31 of the electrically conductive surface 35 may be located on the circular perimeter 220, for example. In certain instances, the circular perimeter 220 can be tangential to the outer perimeter 217 of the electrically conductive surface 35, for example.

Figure 14:
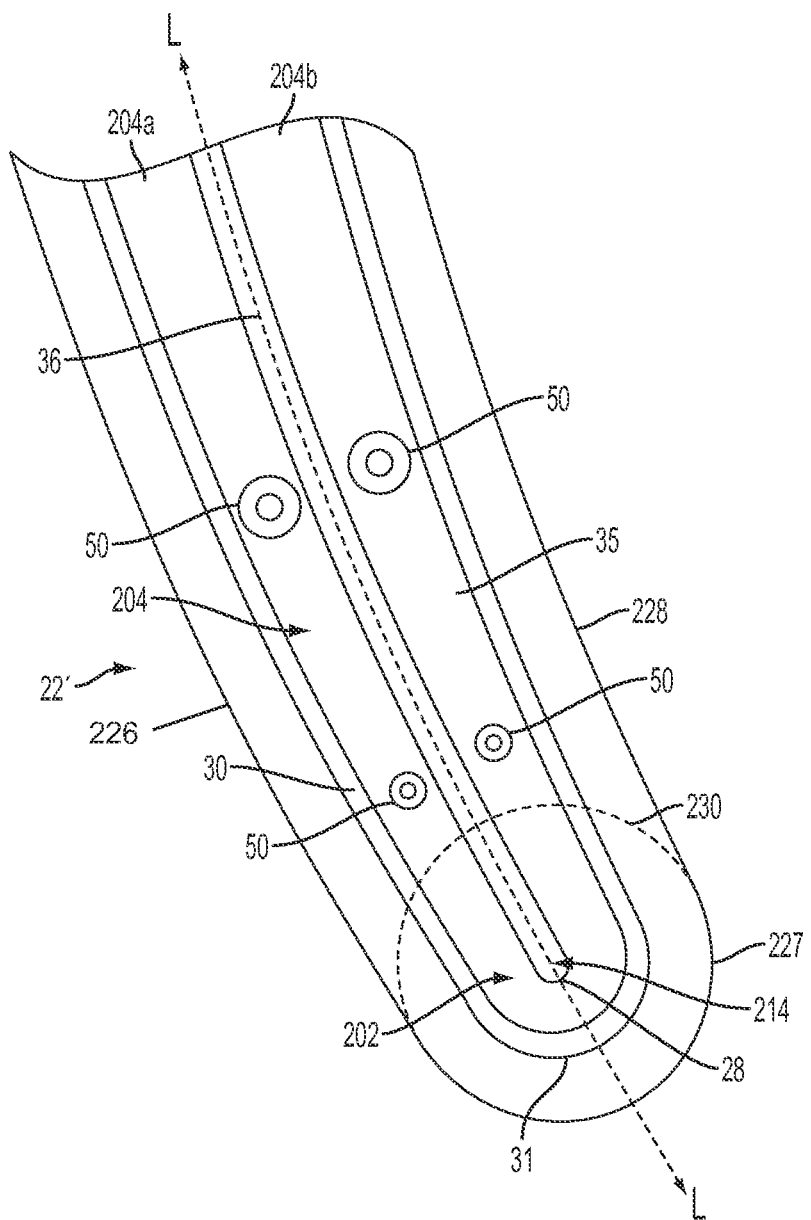
FIG. 14 illustrates a partial top view of a jaw member of the end effector assembly of FIG. 3.

Referring to FIG. 14, in certain instances, the jaw member 22' may include an outer perimeter 227 which may include a peripheral point on the first lateral side of the elongate slot 36 such as, for example, peripheral point 226. In certain instances, the outer perimeter 227 may also include a peripheral point on the second lateral side of the elongate slot 36 such as, for example, peripheral point 228. In certain instances, the distal uninterrupted electrically conductive region 202 can be defined by a circular perimeter 230, for example. It is envisioned that the circular perimeter 230 may encompass the distal uninterrupted electrically conductive region 202. In certain instances, as illustrated in FIG. 14, the circular perimeter 230 may have a diameter comprising a length that is equal, or at least substantially equal, to the distance between the first peripheral point 226 and the second peripheral point 228, for example. In certain instances, as illustrated in FIG. 14, the circular perimeter 230 may encompass the distal end 31 of the electrically conductive surface 35. In certain instances, as illustrated in FIG. 14, the circular perimeter 230 may encompass the distal end 28 of the elongate slot 36. In certain instances, as illustrated in FIG. 14, the circular perimeter 230 can be tangential to the outer perimeter 227 of the jaw member 22'.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical end effector, comprising:
   a cutting member;
   a first jaw member including a first electrode surface, the first electrode surface comprising a first uninterrupted electrically conductive region; and
   a second jaw member, wherein at least one of the first jaw member and the second jaw member is movable relative to the other one of the first jaw member and the second jaw member between an open configuration and an approximated configuration, the second jaw member comprising:
      an elongate slot extending longitudinally along a length of the second jaw member, wherein the elongate slot comprises a distal slot portion terminating at a slot distal end;
      a first lateral side defined by the elongate slot;
      a second lateral side defined by the elongate slot opposite the first lateral side, wherein the cutting member is slidably movable distally between the first lateral side and the second lateral side toward the slot distal end to cut tissue captured between the first jaw member and the second jaw member in the approximated configuration; and
      a second electrode surface terminating at an electrode distal end, the second electrode surface comprising:
         a proximal interrupted electrically conductive region, wherein the elongate slot extends through the proximal interrupted electrically conductive region;
         a plurality of non-conductive stop members disposed on the proximal interrupted electrically conductive region on the first lateral side and the second lateral side of the elongate slot, wherein the plurality of non-conductive stop members are configured to maintain a minimum distance between the first electrode surface and the second electrode surface in the approximated configuration, and wherein the proximal interrupted electrically conductive region is interrupted by the plurality of non-conductive stop members; and
         a distal uninterrupted electrically conductive region distal to the proximal interrupted electrically conductive region, wherein the distal uninterrupted electrically conductive region is defined by a circular perimeter having a radius that is at least double a distance between the slot distal end and the electrode distal end, wherein the circular perimeter encompasses the distal slot portion, wherein the circular perimeter comprises a center proximal to the slot distal end, wherein the distal uninterrupted electrically conductive region is uninterrupted by stop members, wherein in the approximated configuration, the distal uninterrupted electrically conductive region corresponds to the first uninterrupted electrically conductive region of the first jaw member, and wherein the radius of the circular perimeter defining the distal uninterrupted electrically conductive region is quadruple the distance between the slot distal end and the electrode distal end.

2. The surgical end effector of claim 1, comprising a curved shape.

3. The surgical end effector of claim 1, wherein the first jaw member is a large jaw member comprising a length of about 20 mm.

4. A surgical end effector, comprising:
   a cutting member;
   a first jaw member including a first electrode surface comprising an uninterrupted electrically conductive region; and
   a second jaw member, wherein at least one of the first jaw member and the second jaw member is movable relative to the other one of the first jaw member and the second jaw member between an open configuration and an approximated configuration, the second jaw member comprising:
      an elongate slot extending longitudinally along a length of the second jaw member, the elongate slot defining a longitudinal axis aligned with the elongate slot, wherein the elongate slot comprises a distal end, wherein the cutting member is slidably movable relative to the elongate slot along the longitudinal axis toward the distal end of the elongate slot to cut tissue captured between the first jaw member and the second jaw member in the approximated configuration; and
      a second electrode surface extending between a proximal end and a distal end, the second electrode surface comprising:
         a proximal interrupted electrically conductive region, wherein the proximal interrupted electrically conductive region comprises a first length extending distally from the proximal end of the second electrode surface along the longitudinal axis;

a plurality of non-conductive stop members disposed on the proximal interrupted electrically conductive region, wherein the plurality of non-conductive stop members are configured to maintain a minimum distance between the first electrode surface and the second electrode surface in the approximated configuration, and wherein the proximal interrupted electrically conductive region is interrupted by the plurality of non-conductive stop members; and a distal uninterrupted electrically conductive region distal to the proximal interrupted electrically conductive region, wherein the distal uninterrupted electrically conductive region is uninterrupted by non-conductive stop members, wherein the distal uninterrupted electrically conductive region comprises a second length extending proximally from the distal end of the second electrode surface along the longitudinal axis, wherein the second length of the distal uninterrupted electrically conductive region is at least one fifth of the first length of the proximal interrupted electrically conductive region, and wherein in the approximated configuration, the distal uninterrupted electrically conductive region corresponds to the uninterrupted electrically conductive region of the first jaw member.

5. The surgical end effector of claim 4, wherein the second length is one quarter of the first length.

6. The surgical end effector of claim 4, wherein the second length is one third of the first length.

7. The surgical end effector of claim 4, comprising a curved shape.

8. The surgical end effector of claim 4, wherein the first jaw member is a large jaw member comprising a length of about 20 mm.

9. A surgical end effector, comprising:

a cutting member;

a first jaw member including a first electrode surface, the first electrode surface comprising a first uninterrupted electrically conductive region; and a second jaw member, wherein at least one of the first jaw member and the second jaw member is movable relative to the other one of the first jaw member and the second jaw member between an open configuration and an approximated configuration, the second jaw member comprising:

an elongate slot extending longitudinally along a length of the second jaw member, wherein the elongate slot comprises a distal slot portion terminating at a slot distal end;

a first lateral side defined by the elongate slot;

a second lateral side defined by the elongate slot opposite the first lateral side, wherein the cutting member is slidably movable distally between the first lateral side and the second lateral side toward the slot distal end to cut tissue captured between the first jaw member and the second jaw member in the approximated configuration; and a second electrode surface terminating at an electrode distal end, the second electrode surface, comprising:

a proximal interrupted electrically conductive region, wherein the elongate slot extends through the proximal interrupted electrically conductive region, and wherein the proximal interrupted electrically conductive region comprises a first length extending along a longitudinal axis extending through the elongate slot;

a plurality of non-conductive stop members disposed on the proximal interrupted electrically conductive region on the first lateral side and the second lateral side of the elongate slot, wherein the plurality of non-conductive stop members are configured to maintain a minimum distance between the first electrode surface and the second electrode surface in the approximated configuration, wherein the proximal interrupted electrically conductive region is interrupted by the plurality of non-conductive stop members, and wherein the plurality of non-conductive stop members comprises:

a first non-conductive stop member on the first lateral side; and a second non-conductive stop member on the second lateral side, wherein the second non-conductive stop member opposes the first non-conductive stop member defining a distal-most row of non-conductive stop members in the proximal interrupted electrically conductive region; and a distal uninterrupted electrically conductive region, comprising:

a second length that is uninterrupted by non-conductive stop members extending distally from the first length along the longitudinal axis, wherein the second length of the distal uninterrupted electrically conductive region is at least one fifth of the first length of the proximal interrupted electrically conductive region;

a first lateral portion on the first lateral side, wherein the first lateral portion terminates at the first non-conductive stop member of the plurality of non-conductive stop members;

a second lateral portion on the second lateral side, wherein the second lateral portion terminates at the second non-conductive stop member of the plurality of non-conductive stop members; and a distal portion interconnecting the first and second lateral portions, wherein the distal portion terminates at a distal end of the slot distal end, and wherein in the approximated configuration, the distal uninterrupted electrically conductive region corresponds to the first uninterrupted electrically conductive region of the first jaw member.

* * * * *